United States Patent [19]
Hongo et al.

[11] Patent Number: 5,345,944
[45] Date of Patent: Sep. 13, 1994

[54] APPARATUS FOR MEDICAL DIAGNOSIS UTILIZING MASKING OF FIXATION POINT

[75] Inventors: Hitoshi Hongo; Mitsuho Yamada; Kenya Uomori; Hiroshi Yoshimatsu; Keiichi Ueno, all of Kyoto; Mitsuru Fujii, Hokkaido; Shinji Murakami, Hokkaido; Jiro Miyazawa, Hokkaido; Norihito Nakano, Hokkaido; Ryo Fukatsu, Hokkaido; Naohiko Takahata, Hokkaido, all of Japan

[73] Assignee: ATR Auditory and Visual Perception Research Laboratories, Kyoto, Japan

[21] Appl. No.: 31,976

[22] Filed: Mar. 16, 1993

[30] Foreign Application Priority Data

Aug. 12, 1992 [JP] Japan .................. 4-215150

[51] Int. Cl.$^5$ ............................... A61B 5/00
[52] U.S. Cl. ........................................ 128/742
[58] Field of Search ............... 128/731, 732, 745, 782; 351/210, 211

[56] References Cited

U.S. PATENT DOCUMENTS 4,528,989 7/1985 Weinblatt ..................... 128/745
4,889,422 12/1989 Pavlidis ....................... 128/745

FOREIGN PATENT DOCUMENTS

2593381A1 7/1987 France .
1017705 11/1991 PCT Int'l Appl. .............. 128/745

OTHER PUBLICATIONS

"The Significance of Viewing Time in the Visual Fixation Process" by H. Hongo et al., Proceedings of the Annual International Conference of the IEEE Engineering in Medicine and Biology Society, vol. 13, No. 5, 1991, pp. 2156–2158.

"Quantitative Evaluation of Eye Movements as Judged by Sight-Line Displacements" by M. Yamada et al., SMPTE Journal, vol. 95, No. 12, Dec. 1986, pp. 1230–1241.

Primary Examiner—Max Hindenburg
Attorney, Agent, or Firm—Lowe, Price, LeBlanc & Becker

[57] ABSTRACT

When eye movement of a subject is detected by an eye movement detecting portion and head movement of the subject is detected by a head movement detecting portion, a line-of-sight calculating portion calculates the line-of-sight according to the detected outputs therefrom. A portion for generating an image to be presented generates an image as a task and presents the image to a task presenting portion. When a fixation point of the line-of-sight of the subject is determined by a fixation point determining portion, a mask image generated by a masking image generating portion is inserted to the task image by an image synthesizing portion, and it is presented at the task presenting portion. A portion for determining degree of advance of dementia determines degree of advance and possibility of Alzheimer's disease based on the particular movement of the line-of-sight of the subject at that time and on the percentage of correct answer to a prescribed task.

4 Claims, 8 Drawing Sheets

PRESENTED IMAGE

APPARATUS FOR MEDICAL DIAGNOSIS UTILIZING MASKING OF FIXATION POINT

BACKGROUND OF THE INVENTION

1. Field of the Invention

The present invention relates to an apparatus for medical diagnosis utilizing masking of fixation point. More specifically, the present invention relates to an apparatus for medical diagnosis utilizing masking of fixation point in which eye fixation of a subject is detected to enable diagnosis of diseases related to brain function such as Alzheimer's disease.

2. Description of the Background Art

The number of patients suffering from Alzheimer's disease is estimated to be four million in the United States and about a million in Japan. Compared with senile dementia such as cerebrovascular disease popular among Japanese, the cause of Alzheimer's disease is not known, and much effort has made to find the cause so as to enable early diagnosis and early medical treatment. However, it is difficult to discriminate Alzheimer's disease from cerebrovascular disease when there is no typical symptoms. There has been a strong demand of accurate method of discrimination, since development of disease, pharmaceutical treatment and so on are different for these diseases.

Hachinski's ischemic score has been proposed as a method of discriminating these two diseases. According to this ischemic score, a point is given dependent on whether or not the patient has an anamnesis of apoplexy, cerebral infraction or the like and if the points exceeds a prescribed number, it is determined as the cerebrovascular disease, and otherwise it is determined to be Alzheimer's disease. However, discrimination is still difficult by this method if the patient has no such anamnesis.

It has been known that neuropsychological symptom which is considered to be an impairment of "tool disfunction" such as visual cognitive disfunction appears from relatively early period of Alzheimer's disease. In view of this fact, Fujii et al. has reported the following analysis carried out by utilizing eye movement. More specifically, a problem of copying a cube on the right side while watching an original of the cube on the left side is presented. Even a patient who is in the initial stage I of Alzheimer's disease and does not show apparent constructional apraxia is reported to show characteristic symptom similar to a so called Balint syndrome; that is, the patient cannot stare at one point, or more specifically, abnormal distribution of gazing point appears, saccade deviated from both the presented cube and the depicted drawing by the patient is generated, or the point of gazing is fixed at the same point for a long period of time. In Alzheimer's disease, it is supposed from MRI (nuclear magnetic periorbital inspection) that there is caused disfunction of parietal lobe which is related to spatial vision. Accordingly, constructional disfunction derived from degradation in function of the rear association areas with the parietal lobe being the center, degradation of function of positional recognition of a target point or recognition of depth derived from disfunction of external spatial vision such as disfunction of eye movement, disfunction of coordinate transformation system between the coordinate of eye movement system and the coordinate of the center of one's body axis, or visual-motor disfunction, is supposed to be a possible cause of the aforementioned symptoms. As for the extension of fixation time, relation with one's memory has been studied.

SUMMARY OF THE INVENTION

Therefore, an object of the present invention is to provide an apparatus for medical diagnosis utilizing masking of fixation point in which the fixation point is masked for a prescribed time period by a prescribed pattern of a desired size after a lapse of a desired time period, and based on particular movement of the line-of-sight of the patient, on the percentage of correct answer with respect to a prescribed task and so on, objective diagnosis of symptoms related to brain function can be obtained which is not influenced by subjective determination such as caused by interviews, and which does not incur unpresent pain of injection or the like.

Briefly stated, in the present invention, an image which is a task for diagnosis is presented to a subject, the movement of the eyeball of the subject is detected, and based on the movement of the eyeball, the actual movement of the line-of-sight of the subject is calculated. When there is generated a point of fixation in the calculated movement of the line-of-sight, then, after a prescribed period, a desired masking image of a desired size is inserted to the presented image for a prescribed time period. Whether or not the disease is related to brain function is determined in accordance with the movement of the line-of-sight calculated at that time.

Therefore, the present invention enables diagnosis of diseases related to the brain function based not on objective determination such as obtained through interview but on subjective determination, without imposing pain of injection or the like on the patient.

In accordance with a preferred embodiment of the present invention, movement of the head portion of a subject is detected, and the line-of-sight is calculated in accordance with the movement of the head portion and the movement of the eyeball while the subject is gazing at the presented image.

In accordance with a more preferred embodiment, fixation duration distribution, eye movement velocity distribution and movement of the line-of-sight are calculated in accordance with the calculated movement of the line-of-sight, so as to determine whether or not the disease is related to the brain function.

Further, according to a more preferred embodiment, determination as to whether the disease is related to the brain function is given on the basis of the time period in which the masking image is inserted in the presented image and on the percent of correct answer with respect to the task.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
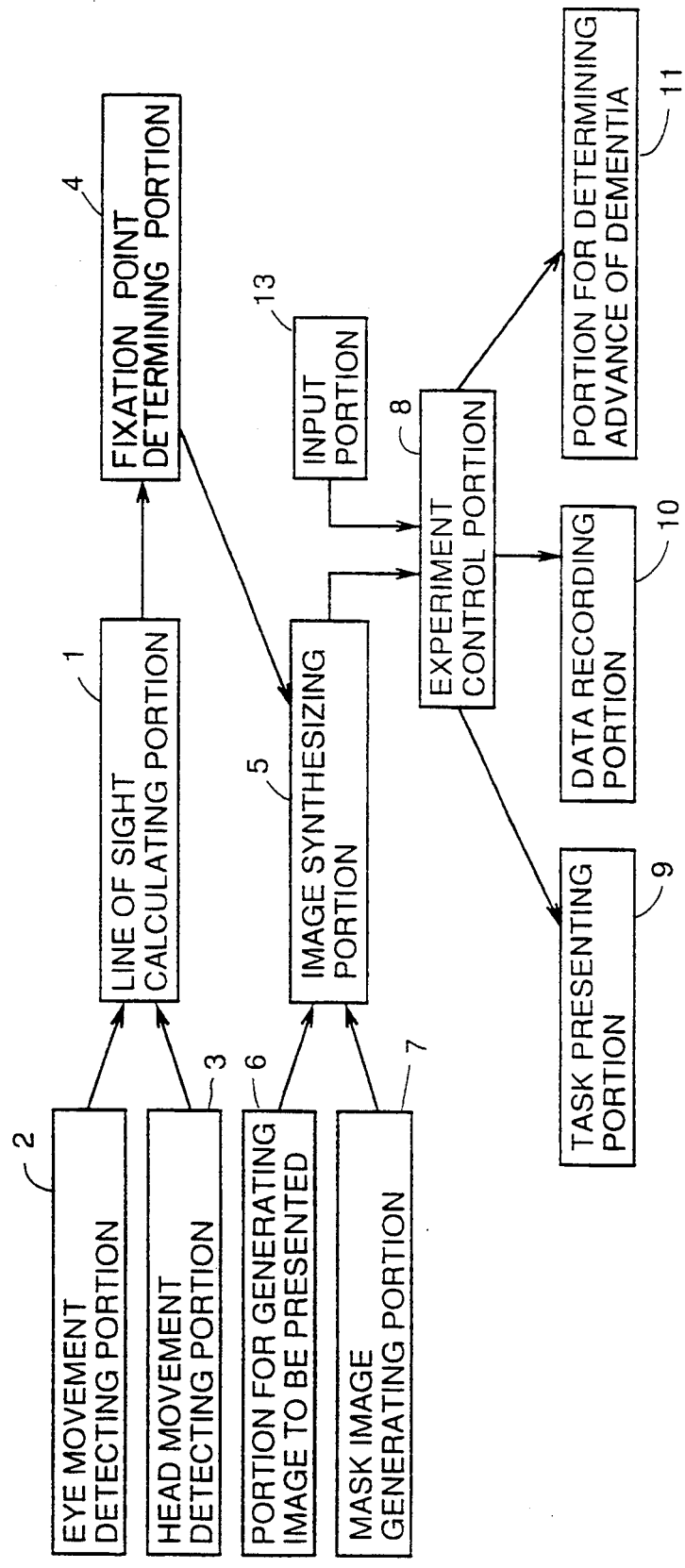
FIG. 1 is a block diagram showing one embodiment of the present invention.

FIG. 1 is a block diagram of one embodiment of the present invention. Referring to FIG. 1, the line-of-sight calculating portion 1 calculates the position of the line-of-sight of the subject. An eye movement detecting portion 2 detects eye movement of the subject and applies the detected output to the line-of-sight calculating portion 1. A head movement detecting portion 3 detects the movement of the head portion of the subject and applies the detected output to the line-of-sight calculating portion 1. When the position of the line-of-sight of the subject is calculated, the line-of-sight calculating portion 1 applies the result of calculation to a fixation point determining portion 4. The fixation point determining portion 4 determines the fixation point of the subject based on the position of the line-of-sight.

A portion 6 for generating an image to be presented generates an image which is to be presented to the subject as a task for diagnosis, and applies the image signal to an image synthesizing portion. A masking image generating portion 7 generates an image signal for masking, for a prescribed time period, the fixation point, at which the subject gazes, of the image presented to the subject with a prescribed masking pattern of a desired size after the lapse of a desired time period. The image signal is applied to the image synthesizing portion.

An experiment control portion 8 presents the image synthesized in the image synthesizing portion 5 at a task presenting portion 9, records data at the data recording portion 10 and determines the advance of dementia by the degree of advance of dementia determining portion 11. A CRT display, for example, is used as the task presenting portion 9 which displays the image synthesized in the image synthesizing portion 5. The data recording portion 10 records data such as the onset of masking, the percentage of correct counting and so on. The degree of advance determining portion 11 determines the possibility of Alzheimer's disease based on the percentage of correct counting. Further, an input portion 13 is connected to the experiment control portion 8. The input portion 13 is for inputting, when the subject counts the image as the task, the counted value.

Figure 2:
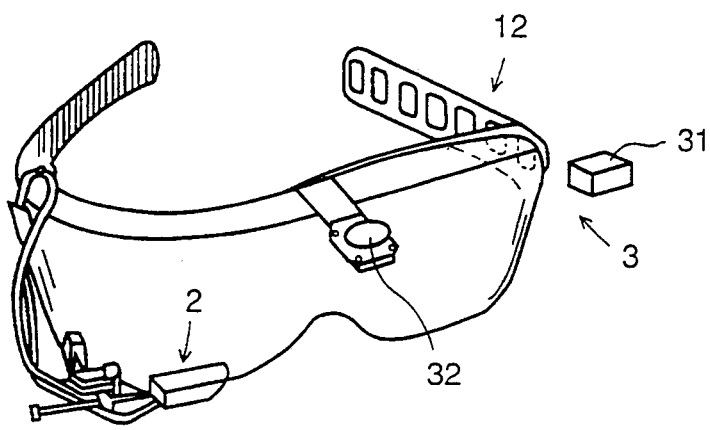
FIG. 2 shows an example in which the eye movement detecting portion and the head movement detecting portion shown in FIG. 1 are attached to goggles.
Figure 3:
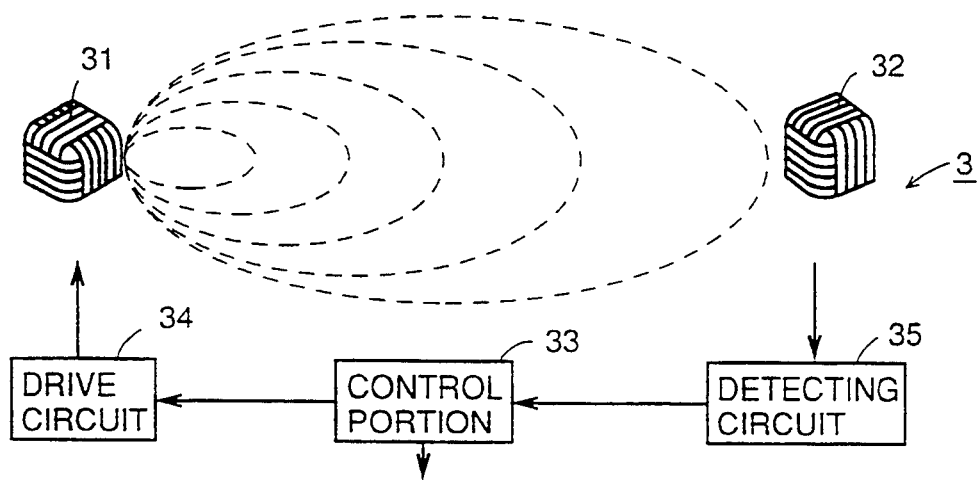
FIG. 3 shows a specific example of the head movement detecting portion.

FIG. 2 shows an example in which the eye movement detecting portion and the head movement detecting portion shown in FIG. 1 are attached to goggles, FIG. 3 shows a specific example of the head movement detecting portion, and FIG. 4 shows a specific example of the eye movement detecting portion.

Figure 4A:
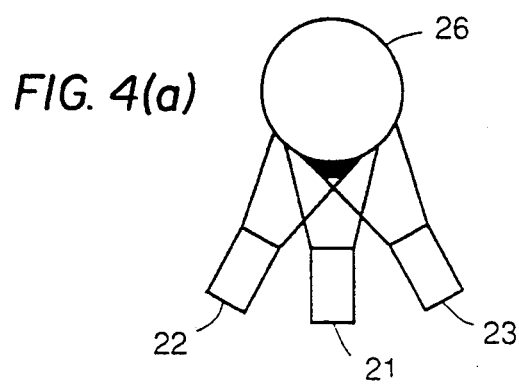
FIGS. 4(a)-(c) show a specific example of the eye movement detecting portion.
Figure 4B:
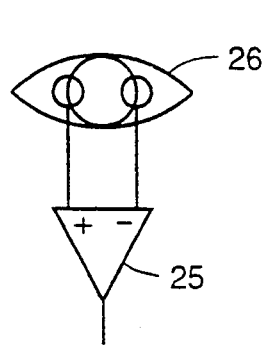
Figure 4C:
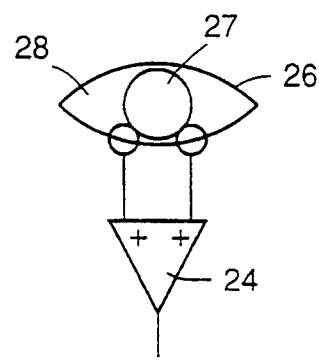

A subject wears the goggles 12 shown in FIG. 2, which has, at a lower portion on one side, the eye movement detecting portion 2 attached. The eye movement detecting portion 2 includes a light emitting diode 21 provided at the center and photodiodes 22 and 23 provided on both sides thereof as shown in FIG. 4(a). A light emitting diode radiating infrared rays having relatively wide directivity of about ±21° is used as the light emitting diode 21, while ones having acute directivity of about ±10° are used as the photodiodes 22 and 23. The light beam emitted from the light emitting diode 21 to the eye ball 26 is reflected from the iris of the eye 27 and from the white of the eye 28 with different reflectivity as shown in FIG. 4 (b) and (c), and the difference in reflectivity is amplified by an operational amplifier 25. If the difference is calculated, a horizontal output (left and right) is obtained as shown in FIG. 4(b), and if the sum is calculated by an operation amplifier 24, a vertical (up and down) output is obtained as shown in FIG. 4(c).

The head movement detecting portion 3 is formed of a magnetic sensor as shown in FIG. 3. More specifically, the head movement detecting portion 3 includes a orthogonal coil serving as a source 31 and an orthogonal coil serving as a sensor 32. In accordance with an instruction from a control portion 33, a driving circuit 34 drives the orthogonal coil of the source 31 to generate a magnetic field. When the subject wearing the head movement detecting portion 3 moves, a voltage is induced in the sensor 32, which voltage is detected by the detecting circuit 35, the detected output therefrom is calculated by the control portion 33, and thus data corresponding to the movement of the head is output.

Figure 5A:
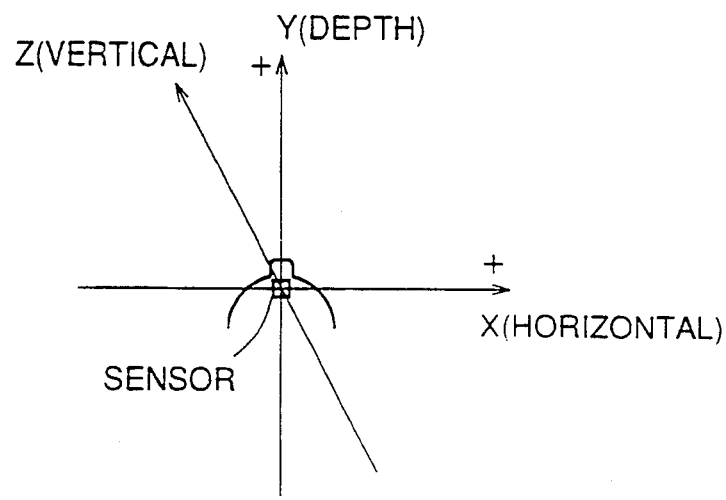
FIGS. 5(a)-(b) show the principal of the head coordinate system with the subject being the center.
Figure 5B:
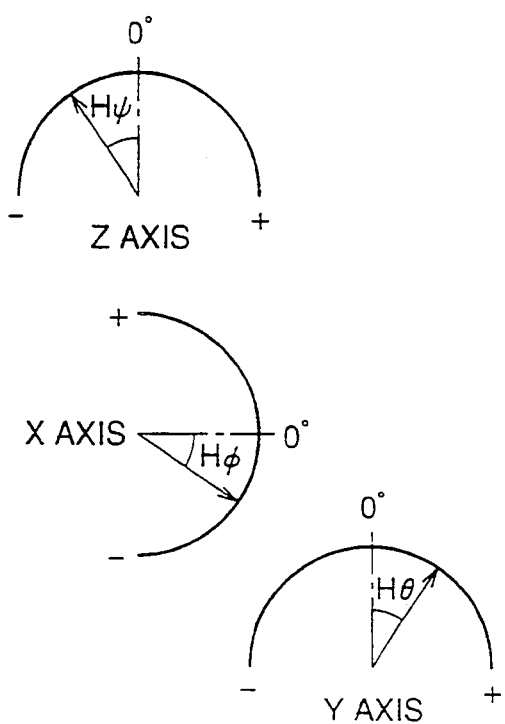

FIG. 5 is an illustration showing the principle of the head coordinate system with the subject being the center. Referring to FIG. 5, the head coordinate system detected by the head movement detecting portion 3 will be described. The head coordinate system includes two systems, that is, XY coordinate system realized by the translational movement of the subject with respect to the object of monitoring such as shown in FIG. 5(a), and a polar coordinate system based on the rotation movement of the head such as shown in FIG. 5(b). The amount of head movement in respective coordinate systems are defined as (Hx, Hy, Hz), (H$\psi$, H$\phi$, H$\theta$). In this embodiment, the direction toward the object of monitoring is represented by the Y axis, the horizontal movement is represented by the X axis and the vertical movement is represented by the Z axis, as an example. H$\phi$ represents the rotation of the X axis, that is, the movement of one's neck upward or downward. H$\theta$ represents the rotation of the Y axis, that is, the movement of inclining ones neck once from the left shoulder to the right shoulder. H$\psi$ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations (1) and (2) are obtained.

$$Ex = 180/\pi \cdot \tan^{-1} Hx/(D+Hy) \tag{1}$$

$$Ey = 180/\pi \cdot \tan^{-1} Hz/(D+Hy) \tag{2}$$

where D: distance from the subject to the point of gazing.

When the neck is inclined by $H\theta$ to the left shoulder or to the right shoulder, the coordinate of the eye movement system rotates. Therefore, the eye movement coordinate system (Xe, Ye) inclined by $H\theta$ must be changed to the coordinate system (Xe', Ye') which is orthogonal to the original object of monitoring.

$$Xe' = Xe \cdot \cos H\theta + Ye \cdot \sin H\theta \quad (3)$$

$$Ye' = -Xe \cdot \sin H\theta + Ye \cdot \cos H\theta \quad (4)$$

The movement of the line-of-sight (Xh, Yh) realized by the head movement is represented by the following equations (5) and (6) derived from the equations (1) and (2).

$$Xh = Ex + H\psi \quad (5)$$

$$Yh = Ey + H\phi \quad (6)$$

Therefore, the movement of the line-of-sight (Vx, Vy) taking the head movement into account is represented by the following equations (7) and (8), from equations (3) to (6).

$$Vx = Xe' + Xh \quad (7)$$

$$Vy = Ye' + Yh \quad (8)$$

By employing the equations (7) and (8) above, the ordinary movement of one's line-of-sight effected by combining head movement and eye movement can be reproduced.

Figure 6:
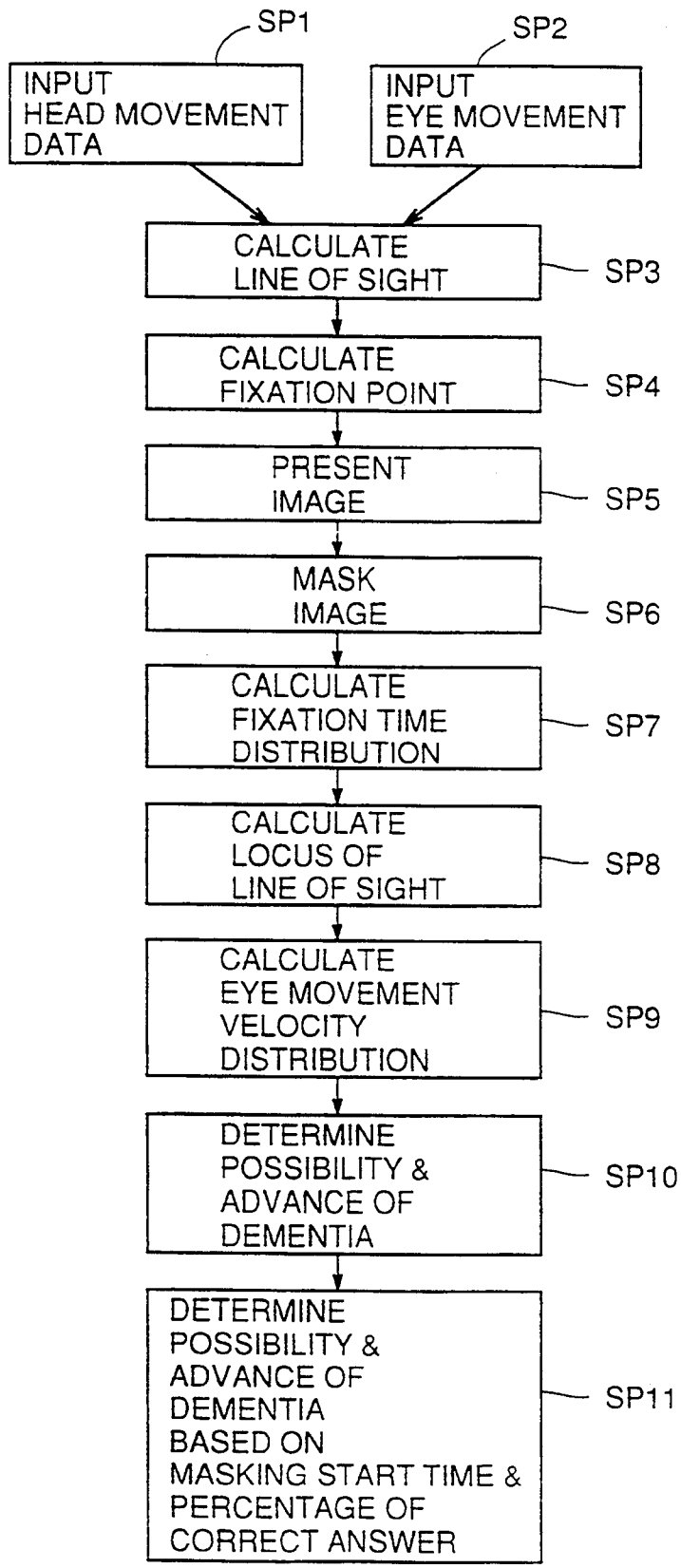
FIG. 6 is a flow chart showing specific operation of one embodiment of the present invention.
Figure 7:
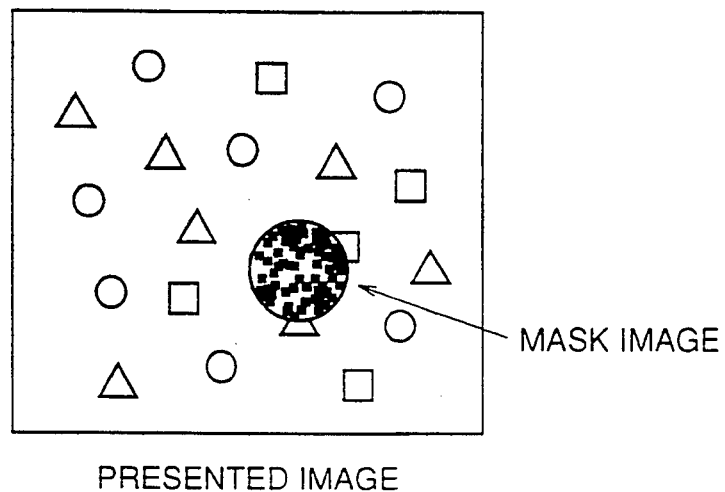
FIG. 7 shows an example of an image in which the fixation point of the line-of-sight of the subject is masked.
Figure 8:
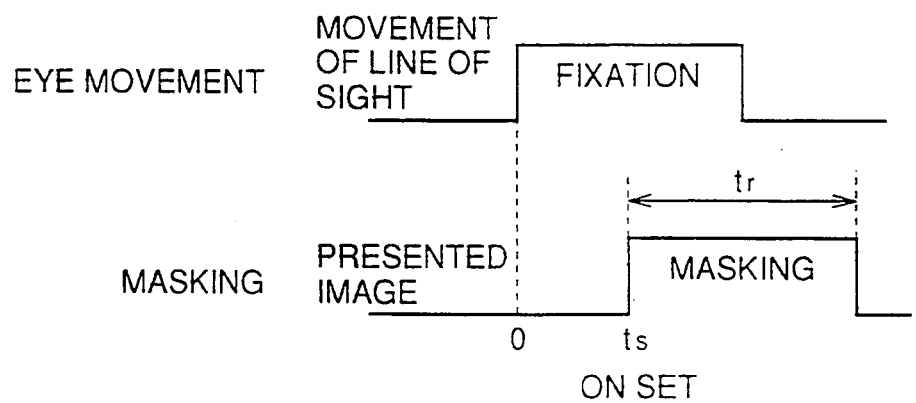
FIG. 8 shows a relation between the eye movement and the masking process.

FIG. 6 is a flow chart showing specific operation of one embodiment of the present invention, FIG. 7 shows an example of the image with the fixation point of the line-of-sight of the subject being masked, and FIG. 8 shows a relation between the time of masking and the time of eye fixation.

A specific operation of one embodiment of the present invention will be described with reference to FIGS. 1 to 8. In step SP1 (simply referred to as SP in the drawings), the amount of head movement (Hx, Hy, Hz), (H$\psi$, H$\phi$, H$\theta$) described with respect to FIG. 5 is applied as the data of head movement from the head movement detecting portion 3 to the calculating portion 1. In step SP2, the eye ball coordinate system (Xe, Ye) is applied as the data of eye movement from the eye movement detecting portion 2 to the calculating portion 1. In step SP3, the calculating portion 1 carries out calculations of the above mentioned equations (1) to (8) in each of the sampling periods i, i+1, i+2 . . . Consequently, the values of H$\psi_i$, H$\phi_i$, H$\theta_i$, Hx$_i$, Hy$_i$, Hz$_i$, X'e$_i$, Y'e$_i$, Vx$_i$ and Vy$_i$ of each sampling period are calculated. The fixation point determining portion 4 calculates the fixation point based on the line-of-sight calculated by the line-of-sight calculating portion 1, in step SP4. In this embodiment, when the next sample is within the scope Dth of fixation point determined by the threshold velocity Vth and the sampling period Ts from the fixation point at present, then this sample is regarded as the same fixation point as the present one. 5°/sec is determined as an exemplary threshold velocity Vth in accordance with the nature of pursuit eye movement. When the sampling period is 10 msec, then Dth = 5°/sec × 0.01 sec = 0.03° = 3'.

The portion 6 for generating the image to be presented generates an image as a task in step SP5. In this embodiment, a task is assigned to the subject that the subject should count the number of ◯ in a pattern including ◯, △ and □. The portion 6 for generating the image to be presented generates image signals of the pattern including circles ◯, triangles △ and squares □. The image signals thus generated are applied to the image synthesizing portion 5, and the experiment control portion 8 applies the image signals to the image presenting portion 9 so that the pattern is displayed. The masking image generating portion 7 generates mask image signals for masking a portion of the task pattern displayed and applies the generated signals to the image synthesizing portion 5, as shown in FIG. 7. The image synthesizing portion 5 inserts the mask image at the fixation point in the task image determined by the fixation point determining portion 4, in step SP6. The experiment control portion 8 applies the image signals with the mask image inserted to the task image to the image presenting portion 9 to be displayed. The timing for masking described above is as shown in FIG. 8. As is apparent from FIG. 8, the pattern image including circles, triangles and squares is presented, after the lapse of time period Ts after the subject gazes the image, the task image is masked by the mask pattern for a prescribed time period Tr, and then the original image is resumed.

The portion for determining degree of advance of dementia 11 receives information related to masking and data of position of the line-of-sight from the experiment control portion 8, calculates the fixation duration distribution in step SP7, calculates the locus of the line-of-sight in step SO8 and calculates eye movement velocity distribution in step SP9, using the onset of masking, the size of the masking, the type of masking and duration of masking as parameters.

Figure 9:
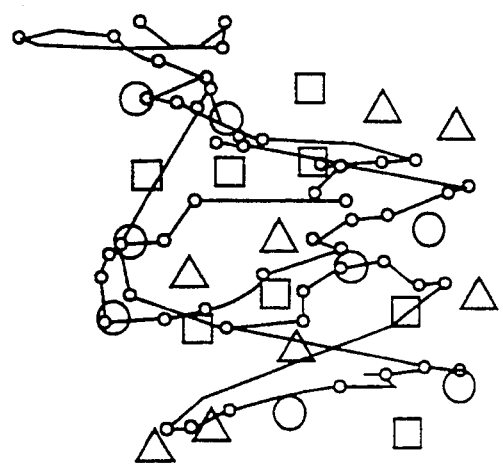
FIG. 9 shows locus of the line-of-sight when a subject suffering from Alzheimer's disease is counting the circles with the fixation point masked for 66 msec at 4°.
Figure 10:
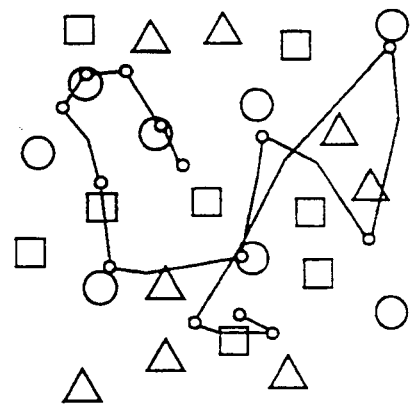
FIG. 10 shows locus of the line-of-sight when a healthy person is counting the circles with the fixation point masked for 66 msec at 4°.

FIG. 9 shows the line-of-sight when the subject suffering from Alzheimer's disease counts the number of circles, and FIG. 10 shows the locus of the line-of-sight when a healthy person counts the number of circles. The aforementioned fixation time distribution represents the distribution of time while the subject is gazing at respective points (the points of circles shown in FIGS. 9 and 10), the locus of the line-of-sight represents a line connecting one point of fixation and the next point of fixation, and the eye movement velocity distribution represents the velocity when the line-of-sight moves from one fixation point to another fixation point. Generally, when a masking pattern of the task image is displayed, the eyeball moves in a quick and leaping movement called saccade in order to avoid masking, and therefore the distribution of the fixation time reduces at this point. However, a patient suffering from Alzheimer's disease having damage on visual function related to spatial vision is incapable of changing the strategy (visual searching) of moving eyeballs as a masking trigger. Therefore, the change in the fixation time distribution such as observed in the case of healthy persons cannot be found, and therefore the degree of advance determining portion 11 determines the possibility and degree of advance of dementia in accordance with the degree of such change. As is apparent from the comparison between FIGS. 9 and 10, in the case of the patient suffering from Alzheimer's disease, there is not a correspondence between the fixation point and the circles in the pattern, as compared with a healthy person. Similar change is observed in the eye movement velocity distribution, and the degree of advance determining portion 11 determines, in step SP10, possibility and the degree of advance of dementia in accordance with the degree of such change.

Figure 11:
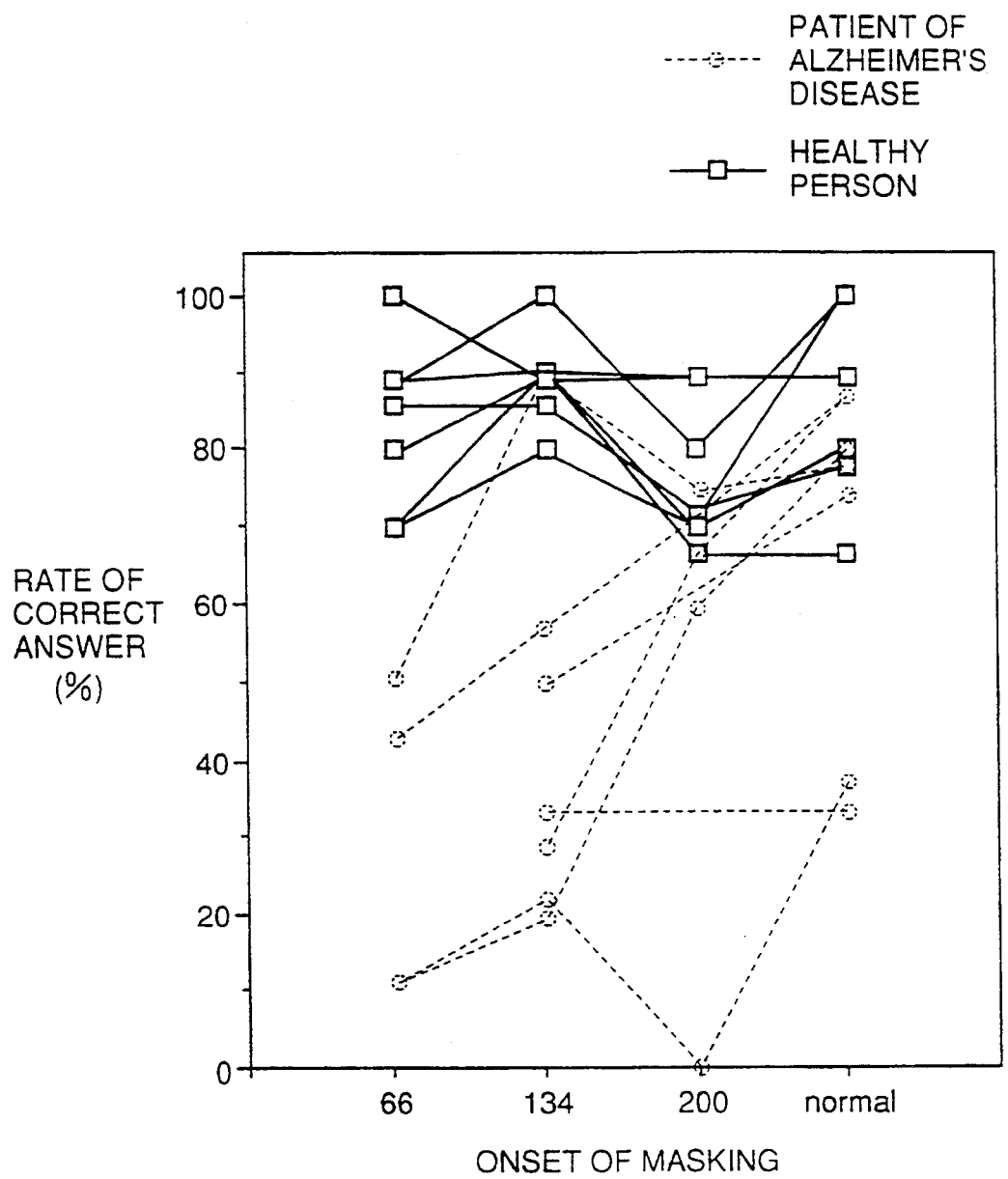
FIG. 11 shows a relation between the percentage of correct counting and the onset of masking.

Then, the degree of advance determining portion 11 determines the possibility and the degree of advance of dementia based on the onset of masking and the percentage of correct answer with respect to the task and on the size of masking in step SP11. FIG. 11 shows a relation between the onset of masking and the percentage of correct answers. Experiments with no mask, (normal) and with mask with the onset of masking changed to 200 msec, 134 msec and 66 msec were carried out in order, the eye movement at the experiments were monitored, and the numbers of counted circles in respective experiment were reported by the subject. When the numbers of circles were input through the input portion 13, and the degree of advance determining portion 11 calculated the percentage of correct answers. The experiment control portion 8 records the data in the manner shown in FIG. 11 by the data recording portion 10 in accordance with the result of calculation.

As is apparent from FIG. 11, the percentage of correct answers is quite high in case of healthy persons, even if the masking is started at 66 msec from the start of gazing. The percentage slightly decreases when the subject is suffering from cerebrovascular disease which is called MID: multi-infarct dementia, which is popular among Japanese. The percentage decreases as the time of presentation becomes shorter when the subject is suffering from Alzheimer's disease. Based on the masking start time at which the percentage falls and on the percentage of correct answers, the degree of advance of the Alzheimer's disease can be determined, and the Alzheimer's disease can be distinguished from other dementia such as MID.

As described above, according to the embodiment of the present invention, eye movement of the subject is detected to calculate the actual movement of the line-of-sight, an image as a task for diagnosis is presented to the subject, a mask image is inserted to the presented image when fixation point is generated in the movement of the line-of-sight and whether or not the disease is related to the brain function is determined in accordance with the output of the line-of-sight. Therefore, diagnosis of diseases related to brain function can be given based on subjective determination, not on objective determination such as obtained by interview, without imposing pain of injection or the like on the subject.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for medical diagnosis employing fixation point masking, enabling diagnosis of a disease related to brain function by detecting line-of-sight of a subject, comprising:
    eye movement detecting means for detecting eye movement of said subject;
    line-of-sight calculating means responsive to a detection output from said eye movement detecting means for calculating actual movement of the line-of-sight of said subject;
    image presenting means for presenting an image as a task for diagnosis to said subject;
    image inserting means for inserting, when a fixation point is generated in spatial movement of the line-of-sight calculated by said line-of-sight calculating means, a desired masking image of an arbitrary size to the image presented by said image presenting means for an arbitrary time period, after the lapse of an arbitrary time period from fixation; and
    determining means responsive to the movement of the line-of-sight calculated by said line-of-sight calculating means when said masking image is inserted to said presented image, determining whether or not the subject is suffering from a disease related to the brain function.

2. The apparatus for medical diagnosis utilizing fixation point masking according to claim 1, further comprising:
    head movement detecting means for detecting movement of the head of said subject; wherein
    said line-of-sight detecting means includes means for calculating actual movement of the line-of-sight of said subject in response to a detection output from said head movement detecting portion and the detection output from said eye movement detecting means when said subject is gazing at said presented image.

3. The apparatus for medical diagnosis utilizing fixation point masking according to claim 1, wherein
    said determining means includes means for determining whether or not the subject is suffering from a disease related to brain function, by calculating fixation duration distribution, eye movement velocity distribution and locus of the line-of-sight in accordance with said calculated movement of the line-of-sight.

4. The apparatus for medical diagnosis utilizing fixation point masking according to claim 1, wherein
    said determining means includes means for determining whether or not the subject is suffering from a disease related to brain function based on the time at which said masking image is inserted to said presented image and on percentage of correct answer to said task.

* * * * *